(12) United States Patent
Zwolinski (10) Patent No.: US 8,088,062 B2
(45) Date of Patent: Jan. 3, 2012

(54) INTERCHANGEABLE ENDOSCOPIC END EFFECTORS

(75) Inventor: Andrew M. Zwolinski, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1134 days.

(21) Appl. No.: 11/770,406

(22) Filed: Jun. 28, 2007

(65) Prior Publication Data

US 2009/0005638 A1 Jan. 1, 2009

(51) Int. Cl.
  *A61B 1/00* (2006.01)
  *A61B 1/04* (2006.01)
  *A61B 17/00* (2006.01)
(52) U.S. Cl. ......... 600/106; 600/104; 600/127; 606/205
(58) Field of Classification Search .................. 600/104, 600/106, 127, 129, 107; 606/142, 143, 205–209, 606/220; 483/47, 59
See application file for complete search history.

(56) References Cited

U.S. PATENT DOCUMENTS

| | | | |
|---|---|---|---|
| 5,755,713 A * | 5/1998 | Bilof et al. ......................... 606/1 |
| 6,059,719 A * | 5/2000 | Yamamoto et al. ........... 600/127 |
| 6,309,397 B1 | 10/2001 | Julian et al. |
| 6,626,824 B2 | 9/2003 | Ruegg et al. |
| 6,770,081 B1 | 8/2004 | Cooper et al. |
| 6,860,878 B2 * | 3/2005 | Brock .............................. 606/1 |
| 6,869,395 B2 | 3/2005 | Page et al. |
| 6,884,213 B2 | 4/2005 | Raz et al. |
| 2004/0152941 A1 | 8/2004 | Asmus et al. |
| 2004/0181169 A1 * | 9/2004 | Diamond et al. ............. 600/564 |
| 2005/0250984 A1 | 11/2005 | Lam et al. |

OTHER PUBLICATIONS

International Search Report, International Application No. PCT/US08/066627, dated Oct. 31, 2008.

* cited by examiner

*Primary Examiner* — Matthew J Kasztejna
*Assistant Examiner* — Ryan Henderson
(74) *Attorney, Agent, or Firm* — Nutter McClennen & Fish LLP

(57) ABSTRACT

Methods and devices are provided for performing various procedures using interchangeable end effectors. In general, the methods and devices allow a surgeon to remotely and selectively interchange various surgical end effectors within a patient's body, thus allowing the surgeon to perform various procedures without the need to remove the device from the patient's body. In one embodiment, a modular device is provided having an insertion device and a cartridge containing a plurality of end effectors coupled to or formed on the insertion device. The cartridge can be configured to move between various positions to allow an instrument shaft to be selectively mated to one of the various end effectors contained within the cartridge. For example, the cartridge can be moved to a desired position, and an instrument shaft can be advanced into a chamber in the cartridge to engage and remove an end effector from the cartridge, thus allowing the end effector to be used to perform a surgical procedure. Once complete, the instrument shaft can be retracted relative to the cartridge to return the end effector into its original chamber in the cartridge. The cartridge can then be repositioned to allow the shaft to engage and utilize another end effector.

20 Claims, 5 Drawing Sheets

INTERCHANGEABLE ENDOSCOPIC END EFFECTORS

FIELD OF THE INVENTION

The present invention relates to methods and devices for performing surgical procedures using interchangeable end effectors.

BACKGROUND OF THE INVENTION

Versatility and mobility in medical devices, particularly in medical devices to be used internally of a patient, are important, and can be especially important in minimally invasive surgical procedures. Minimally invasive surgical procedures are typically conducted through small ports, in contrast to the larger incisions typical of open surgery, and they are desirable because such procedures can reduce pain and provide relatively quick recovery times as compared with conventional open medical procedures. There are various terms used to describe minimally invasive procedures, including endoscopic, laparoscopic, thoracoscopic, and the like. The term endoscopic is used herein to generally refer to these various procedures.

Typical state of the art endoscopic procedures demand new families of instruments, and a variety of custom-designed instruments have been created for such procedures. Their common feature has been the ability to be passed through the cannula of a trocar, or other small opening into the body, or through a natural orifice of the body, such as through a working channel of an endoscope disposed within a body lumen. One drawback to current procedures, however, is that they often require the use of multiple tools having different types of end effectors. Each tool has to be individually passed into the body, manipulated to perform a procedure, and then removed to allow a second tool to be introduced. As a result, the time required for a surgeon to perform the procedure as well as the costs of the procedure are significantly increased.

Accordingly, there remains a need for methods and devices for performing surgical procedures using interchangeable end effectors, and in particular using end effectors that can be selectively interchanged within the body.

SUMMARY OF THE INVENTION

The present invention generally provides methods and devices for performing surgical procedures using interchangeable end effectors. In one embodiment, a modular endoscopic surgical device is provided and includes an insertion device having a cartridge movably disposed on a distal portion thereof and having a plurality of chambers formed therein. The device can also include a plurality of surgical end effectors with each end effector being disposed within a chamber in the cartridge, and an instrument shaft adapted to interchangeably mate with the plurality of surgical end effectors.

The instrument shaft can have a variety of configurations, but in one exemplary embodiment the instrument shaft includes a first member adapted to selectively engage a surgical end effector disposed within a chamber, and a second member adapted to translate relative to the first member to displace the surgical end effector from the chamber. Movement of the first and second members relative to one another can also be adapted to actuate the surgical end effector. In another embodiment, the instrument shaft can be longitudinally slidably coupled to the insertion device. For example, the instrument shaft can be disposed through an accessory channel coupled to the insertion device.

The cartridge can also have a variety of configurations. In one embodiment, the cartridge can be rotatably disposed around a distal portion of the insertion device. The device can optionally include an actuator movably coupled to the insertion device and adapted to rotate the cartridge relative to the insertion device to selectively position a chamber in alignment with the instrument shaft. In another embodiment, the cartridge can be longitudinally slidable along a longitudinal axis of the insertion device.

Each end effector can also have various configurations. In one embodiment, each end effector can include a clevis, and the first member can be adapted to engage a proximal portion of the clevis. The second member can be movable between a proximal position in which the second member is retracted relative to the first member to allow the first member to be disengaged from the end effector, and a distal position in which the second member is advanced over the first member to lock the first member into engagement with an end effector.

In another embodiment, each end effector can be movable within the chamber between a first position in which at least one pin on the end effector extends into at least bore formed in the chamber to retain the end effector in the chamber, and a second position in which the at least one pin on the end effector is retracted into the end effector to allow the end effector to be released from the chamber. Each end effector can also include a retaining element slidably mated to and disposed around the clevis. The pin(s) can be disposed within a thru-hole(s) extending through the retaining element. In an exemplary embodiment, the pin(s) is biased into the end effector.

In yet another embodiment, a modular endoscopic surgical device is provided and includes an elongate shaft having a cartridge coupled thereto and having a plurality of chambers formed therein. A plurality of end effectors can be disposed within the plurality of chambers, and each end effector can have an engagement mechanism movable between a locked position, in which the end effector is retained within the chamber, and a released position in which the end effector is released from the chamber. The device can also include an instrument shaft adapted to selectively engage each end effector and to effect movement of the end effector relative to the chamber to cause the engagement mechanism to move between the locked and released positions. In an exemplary embodiment, the instrument shaft includes an inner tube adapted to engage an end effector, and an outer tube slidably disposed over the inner tube and adapted to lock the inner tube into engagement with the end effector. When the inner tube is in locked engagement with an end effector, the inner tube can be adapted to move relative to the outer tube to cause the engagement mechanism on the end effector to move between the locked and released positions.

Exemplary surgical methods are also provided, and in one embodiment the method can include inserting an insertion member through a body lumen, such as a tortuous lumen, to position a cartridge located on the insertion member adjacent to a surgical site. The cartridge can have a plurality of chambers formed therein and a plurality of surgical end effectors, with each surgical end effector being retained within one of the plurality of chambers. A first elongate shaft can be advanced relative to the insertion member to cause the first elongate shaft to engage a first one of the plurality of surgical end effectors, and a second elongate shaft can be advanced relative to the first elongate shaft to cause the second elongate shaft to displace the first one of the plurality of surgical end effectors from the chamber. The method can also include, prior to advancing the first elongate shaft, positioning the cartridge in a first position to align a first one of the plurality of surgical end effectors with the first and second elongate shafts. In other aspects, the method can include performing a medical procedure using the first one of the plurality of surgical end effectors, retracting the first and second elongate shafts to return the first one of the plurality of surgical end effectors to the chamber within the cartridge, advancing the first elongate shaft relative to the insertion member to cause the first elongate shaft to engage a second one of the plurality of surgical end effectors, and advancing the second elongate shaft relative to the first elongate shaft to cause the second elongate shaft to displace the second one of the plurality of surgical end effectors from the chamber. Prior to advancing the first elongate shaft relative to the insertion member to cause the first elongate shaft to engage a second one of the plurality of surgical end effectors, the cartridge can be positioned in a second position to align the second one of the plurality of surgical end effectors with the first and second elongate shafts. In other embodiments, after advancing the first elongate shaft relative to the insertion member to cause the first elongate shaft to engage a first one of the plurality of surgical end effectors, the method can include retracting the first elongate shaft relative to the second elongate shaft to cause the second elongate shaft to lock the first elongate shaft into engagement with the end effector.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for performing various procedures using interchangeable end effectors. In general, the methods and devices allow a surgeon to remotely and selectively interchange various surgical end effectors within a patient's body, thus allowing the surgeon to perform various procedures without the need to remove the device from the patient's body. In particular, a cartridge containing a plurality of end effectors can be formed on or mated to an insertion device, such as a catheter, endoscope, or any other elongate member adapted to be introduced into a patient's body. The cartridge can be configured to move between various positions to allow an instrument shaft to be selectively mated to one of the various end effectors contained within the cartridge. For example, the cartridge can be moved to a desired position, and an instrument shaft can be advanced into a chamber in the cartridge to engage and remove an end effector from the cartridge, thus allowing the end effector to be used to perform a surgical procedure. Once complete, the instrument shaft can be retracted relative to the cartridge to return the end effector into its original chamber in the cartridge. The cartridge can then be repositioned to allow the shaft to engage and utilize another end effector. This is particularly advantageous as the device allows for the use of multiple end effectors during a single surgical procedure without the need to remove the instrument shaft from the patient's body to change the end effectors. All end effectors can be interchangeably mated to the instrument shaft within the patient's body.

A person skilled in the art will appreciate that the devices disclosed herein can be configured for use in numerous surgical procedures. By way of non-limiting example, the devices can be used in endoscopic procedures, in which the device is introduced into the body through a natural orifice, such as the oral, nasal, anal, or vaginal cavities. For example, the insertion device, or portions thereof, can be flexible and it can be advanced intralumenally, e.g., through the esophagus or colon, to position a distal end of the device at a surgical site. The surgical site can be located within the body lumen or within a body cavity or organ accessed via the body lumen. The devices can also be used in laparoscopic procedures, in which the device is introduced percutaneously. For example, the insertion device can be rigid or flexible and it can be inserted through tissue to access a body cavity, such as the peritoneal cavity, or to access a hollow organ or a body lumen. The modular devices can also be used in procedures that include a combination of endoscopic and laparoscopic techniques, as well as in open surgical procedures.

A person skilled in the art will also appreciate that the term "end effector" as used herein is intended to include any device that is configured to affect a particular surgical outcome. By way of non-limiting example, suitable end effectors include mono-polar coagulators and probes, bi-polar coagulators and probes, graspers, biopsy forceps, clipping devices, retractors, scissors, band ligators, suction devices, needles, needle knives and other cutting devices, sphincterotomes, snares, irrigation devices, marking devices, etc. Various techniques for actuating the end effectors can also be used. By way of non-limiting example, U.S. patent application Ser. No. 11/693,976 entitled "Detachable End Effectors" by Jonathan A. Coe et al. discloses various end effectors and various techniques for actuating the end effectors using a detachable actuation mechanism. This application is hereby incorporated by reference in its entirety.

Figure 1A:
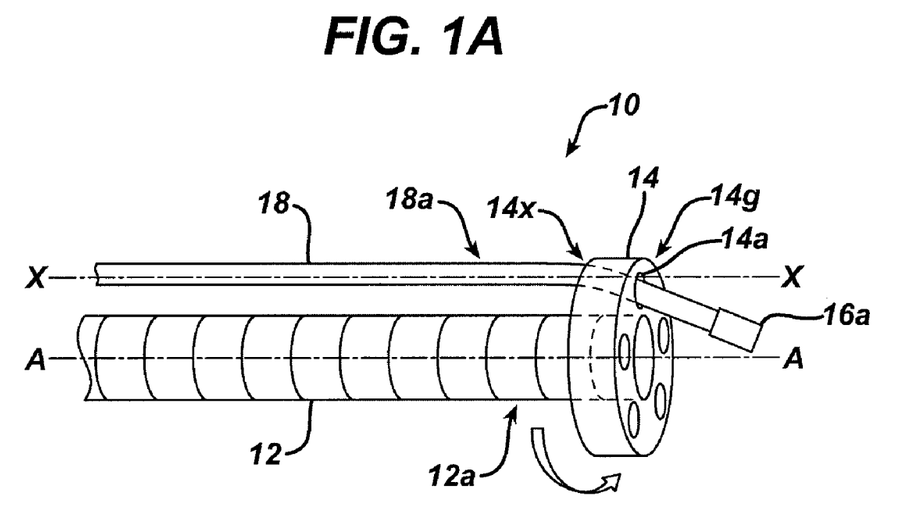
FIG. 1A is a side perspective view of one embodiment of distal portion of a modular endoscopic surgical device having an insertion member, a rotatable cartridge for holding a plurality of end effectors, and an instrument shaft for mating to the plurality of end effectors.

FIG. 1A illustrates one exemplary embodiment of a modular surgical device 10 that includes an insertion device 12 having a cartridge 14 disposed on a distal end 12a thereof for retaining a plurality of end effectors. The insertion device can have a variety of configurations, and as indicated above it can be adapted for use in various surgical procedures. The insertion device 12, or portions thereof, can be rigid, flexible, or semi-flexible, and it can be solid or can include one or more lumens extending therethrough. In an exemplary embodiment, the insertion device 12 is an endoscope, or a sleeve adapted to be disposed over an endoscope. The proximal end (not shown) of the device 12 can be configured to remain outside of the patient's body while the distal end 12a of the device 12 is disposed within the body adjacent to a surgical site. Various exemplary insertion devices are disclosed in U.S. Publication Nos. 2003/0176766, 2003/0176767, 2004/0230095, 2004/0230096, and 2004/0230097, each of which is herein incorporated by reference in its entirety.

Figure 1B:
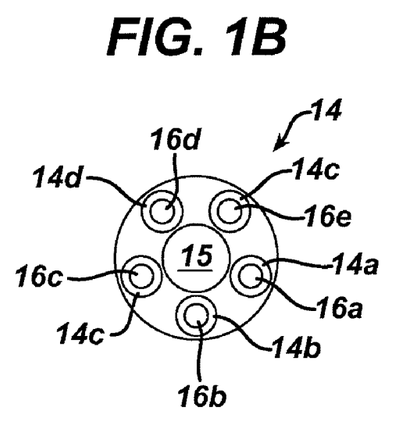
FIG. 1B is an end view of the cartridge of FIG. 1A showing a plurality of end effectors disposed within a plurality of chambers in the cartridge.

The particular configuration of the cartridge 14 can also vary, but it is preferably adapted to retain two or more end effectors therein. In the illustrated embodiment, the cartridge 14 has a generally cylindrical shape and includes several bores or chambers extending therethrough with each chamber being adapted to hold a single end effector. FIG. 1B illustrates five chambers 14a, 14b, 14c, 14d, 14e spaced radially around the cartridge 14 for holding five end effectors 16a, 16b, 16c, 16d, 16e. The chambers 14a-e extend from a proximal surface 14x to a distal surface 14y of the cartridge 14 such that a longitudinal axis of each chamber 14a-e can be longitudinally aligned with a longitudinal axis X of an instrument shaft 18 extending adjacent to the insertion device 12. A person skilled in the art will appreciate that the number of chambers can vary depending on the number of end effectors to be used, as well as the particular configuration of the cartridge and the insertion device to which the cartridge is attached.

Figure 1C:
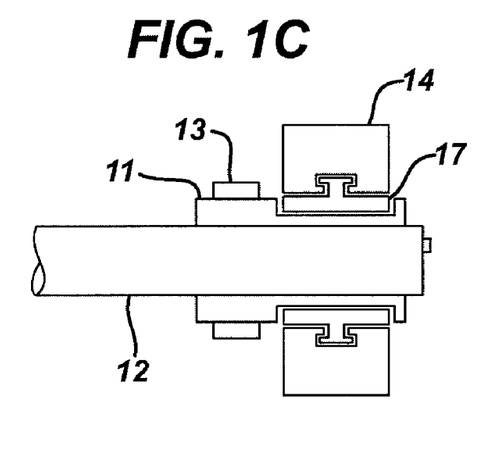
FIG. 1C is a side cross-sectional view of one embodiment of a mating technique for rotatably mating a the cartridge of FIG. 1A to the insertion device of FIG. 1A.

The cartridge 14 can be mated to or formed on the insertion device 12 at various locations and the particular location can vary depending on the configuration of the cartridge 14. In the embodiment shown in FIG. 1A, the cartridge 14 includes a central bore 15 extending therethrough. The central bore 15 is configured to receive the distal end 12a of the insertion device 12 to thereby mate the cartridge 14 to the insertion device 12. As a result, the chambers 14a-e will be disposed around the distal end 12a of the insertion device 12. Various techniques can be used to mate the cartridge 14 to the insertion device 12, but in an exemplary embodiment the cartridge 14, or at least a portion thereof containing the chambers 14a-e, is rotatably mated to the insertion device 12. Such a configuration will allow each chamber 14a-e in the cartridge 14 to be aligned with an instrument shaft 18 extending longitudinally along the insertion device 12, as will be discussed in more detail below. A person skilled in the art will appreciate that various techniques can be used to rotatably mate the cartridge 14 to the insertion device 12. In one embodiment, as shown in FIG. 1C, the cartridge 14 includes a central ring 17 that is disposed within the inner lumen of the cartridge 14 and that is rotatably mated to the cartridge 14, e.g., using a keyed connection, such as a keyed pin and groove. A sheath or sleeve, such as an elastomeric sheath 11, extends proximally from the central ring 17, and the sheath 11 is sized to fit around and receive the distal end 12a of the insertion device 12 therein. A clip, such as a c-clip 13, or any other fastening element, can be positioned around the sheath 11 and the insertion device 12 to mate the sheath 11 to the insertion device 12. In use, the keyed connection between the central ring 17 and the cartridge 14 allows the cartridge 14 to rotate relative to the insertion device 12. A person skilled in the art will appreciate that a variety of other techniques can be used, and that the cartridge 14 can be directly mated to the insertion device 12, or to various other devices that mate to an insertion device.

FIG. 1A also illustrates an instrument shaft 18 for selectively mating to each end effector 16a-e in the cartridge 14. The configuration of the instrument shaft 18 can vary. It can be flexible, semi-rigid, or rigid, and it can be solid or hollow. The instrument shaft 18 can also include features to facilitate engagement to the end effector 16a-e, and actuation or operation of the end effector 16a-e. The particular features will vary depending on the particular configuration of the end effector 16a-e, and an exemplary instrument shaft 18 will be discussed in more detail below. In use, the instrument shaft 18 is preferably configured to extend longitudinally adjacent to the insertion device 12 such that the longitudinal axis X of the instrument shaft 18 extends substantially parallel to the longitudinal axis A of the insertion device 12. The distal end 18a of the instrument shaft 18 can, however, have a bend or it can be configured to bend or move out of the axis X to position an end effector mated thereto relative to a surgical site. While not shown, the instrument shaft 18 can optionally be disposed through a sheath or accessory channel coupled to the insertion device 12. Exemplary configurations for the accessory channel are disclosed in more detail in U.S. Publication Nos. 2003/0176766, 2003/0176767, 2004/0230095, 2004/0230096, and 2004/0230097, each of which is herein incorporated by reference in its entirety. The distal end 18a of the instrument shaft 18 can be configured to engage an end effector 16a-e and to release the end effector 16a-e from its chamber 14a-e, as will be discussed in more detail below. In order to allow mating between the instrument shaft 18 and an end effector 16a-e, the cartridge 14 can be rotated to selectively position a chamber 14a-e into longitudinal alignment with the instrument shaft 18. Alternatively, the instrument shaft 18 can include one or more bends or curves formed therein to allow the instrument shaft 18 to be inserted into a chamber 14a-e in the cartridge 14. In other embodiments, the instrument shaft 18 can be disposed through a lumen in the insertion device 12. In such an embodiment, the cartridge 14 can be positioned to allow the chambers 14a-e to be aligned with the lumen in the insertion device 12.

Figure 2:
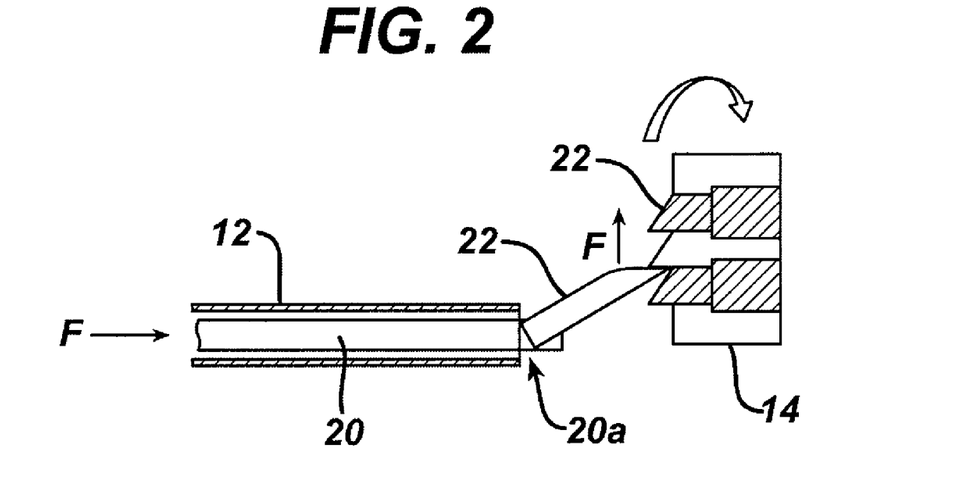
FIG. 2 is a side partially cross-sectional view of one embodiment of an actuation mechanism for rotating the cartridge of FIGS. 1A and 1B.

The device 10 can also include features to facilitate rotation of the cartridge 14 relative to the insertion device 12 and instrument shaft 18. In an exemplary embodiment, the device 10 includes an actuator having a proximal end that remains outside of the body for manipulation, and a distal end that couples to the cartridge 14 for allowing remote rotation of the cartridge 14 (i.e., rotation from outside of the patient's body). FIG. 2 illustrates one exemplary of an actuation mechanism for rotating the cartridge 14 relative to the distal end 12a of the insertion device 12. In this embodiment, the actuation mechanism is in the form of a push rod 20 that translates or slides longitudinally along the longitudinal axis of the insertion device 12. The push rod 20 can be disposed through a lumen in the insertion device 12, as shown, or it can extend along an outer surface of the insertion device 12. The distal end 20a of the push rod 20 can include an arm 22 pivotally mated thereto and adapted to engage teeth 24 formed on the proximal-facing surface of the cartridge 14. Translation of the push rod 20 in a distal direction can cause the arm 22 to engage the teeth 24 on the cartridge 14 and to apply a force to the cartridge 14 to cause it to rotate about its central axis. Proximal movement of the push rod 20 will allow the arm 22 to retract and to move over the teeth 24 to reposition the arm 22 in its initial position. Movement of the push rod 20 between the proximal and distal positions can be repeated to position a desired chamber 14-ae into alignment with the instrument shaft 18. In an exemplary embodiment, the push rod 20 and teeth 22 are configured such that the cartridge 14 rotates a predetermined distance with each actuation of the push rod 20 to thereby always maintain one chamber 14a-e in alignment with the instrument shaft 18.

Figure 3:
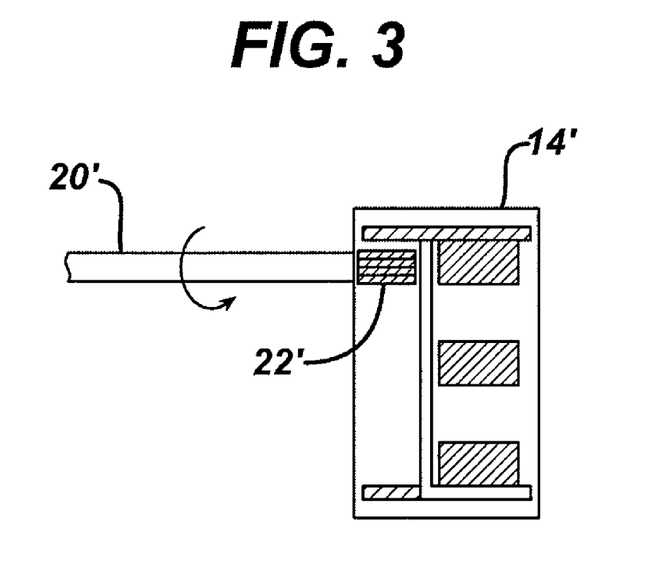
FIG. 3 is a side partially cross-sectional view of another embodiment of an actuation mechanism for rotating the cartridge of FIGS. 1A and 1B.

FIG. 3 illustrates yet another embodiment of a technique for rotating the cartridge 14. In this embodiment, the actuation mechanism is adapted to rotate relative to the insertion device 12' to cause rotation of the cartridge 14'. In particular, the actuation mechanism is in the form of a torsionally rigid coil 20' having gear teeth 22' formed on a distal end thereof. The cartridge 14' can include corresponding teeth (not shown) formed around an inner surface thereof such that rotation of the coil 20' will cause corresponding rotation of the cartridge 14'. A person skilled in the art will appreciate that a variety of other techniques can be used to rotate the cartridge relative to the insertion device.

Figure 4A:
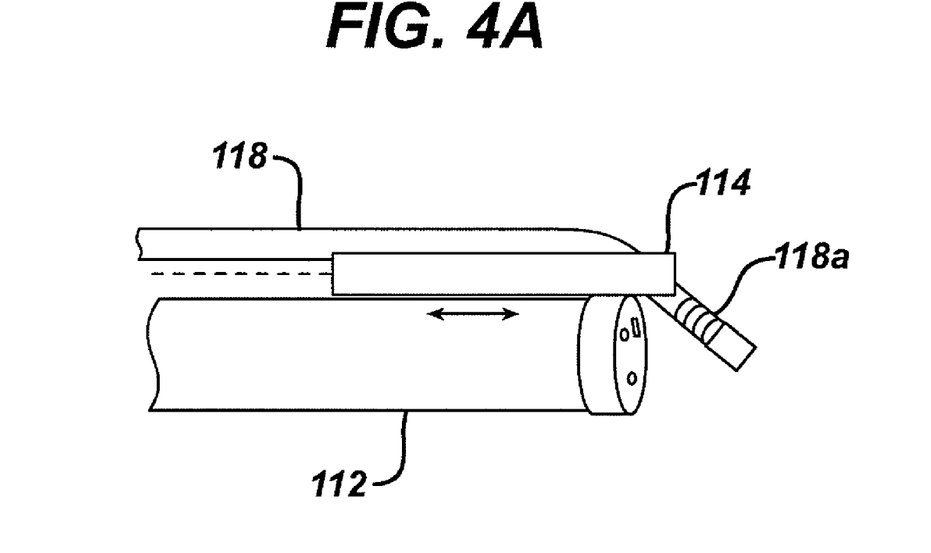
FIG. 4A is a side, perspective view of yet another embodiment of a distal portion of a modular endoscopic surgical device having an insertion member, a translating cartridge for holding a plurality of end effectors, and an instrument shaft for mating to the plurality of end effectors.
Figure 4B:
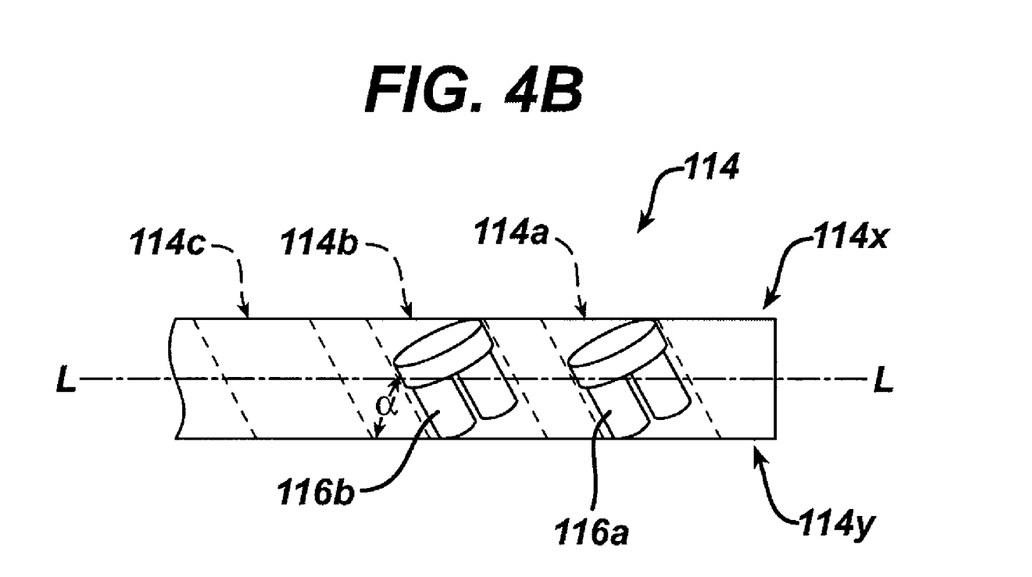
FIG. 4B is a side cross-sectional view of the cartridge of FIG. 4A showing a plurality of end effectors disposed within a plurality of chambers in the cartridge.

FIG. 4A illustrates another embodiment of a cartridge for retaining a plurality of end effectors. In this embodiment, the cartridge 114 has a generally elongate or linear configuration. The particular cross-sectional shape of the cartridge 114 can vary, and it can be circular, square, or any other shape. Similar to the embodiment of FIGS. 1A and 1B, the cartridge 114 can also include two or more chambers for retaining two or more end effectors. FIG. 4B illustrates three chambers 114a, 114b, 114c extending through the cartridge 114 from a top surface 114x to a bottom surface 114y of the cartridge 114 for holding three end effectors (only two end effectors 116a, 116b are shown). In this embodiment, the chambers 114a-c extend at an angle a relative to a longitudinal axis L of the cartridge 114 to allow an instrument shaft 118 having a bent or angled distal end 118a to be inserted therethrough and to extend into a viewing region of the insertion device 112. The cartridge 114 can be mated to the insertion device 112 at various positions, but in the illustrated embodiment the cartridge 114 is positioned to extend longitudinally adjacent to the insertion device 112 such that the cartridge 114 and insertion device 112 are generally parallel to one another. The cartridge 114 can also be longitudinally slidably mated to an outer sidewall of the insertion device 112 to allow each chamber 114a-c to be selectively aligned with the distal end 118a of the instrument shaft 118. Various mating techniques can be used to slidably mate the cartridge 114 to the insertion device 112. For example, one of the cartridge 114 and insertion device 112 can include a track formed therein and the other one of the cartridge 114 and insertion device 112 can include a rail that slides within the track. A person skilled in the art will appreciate that a variety of other techniques can be used to slidably mate the cartridge 114 to the insertion device 112.

As indicated above, the present invention also provides techniques for releasably retaining an end effector in a cartridge chamber, and for actuating the end effector, e.g., opening and closing opposed jaws, etc. FIGS. 5A-7B illustrate one exemplary embodiment of one such technique. In general, the end effector 50 includes a clevis 52 formed on a proximal end thereof, and a retaining element 54 disposed around the clevis 52. The clevis 52 can have a variety of configurations, but in general it has an elongate shape with a proximal end 52a adapted to mate to a distal end 18a of an instrument shaft 18, and a distal end 52b having a surgical instrument formed thereon or mated thereto. In the illustrated embodiment, the distal end 52b includes a pair of jaws 56a, 56b pivotally coupled thereto. A person skilled in the art will appreciate that the clevis 52 can have a variety of other configurations, and that other components can be used in place of a clevis 52 depending on the particular configuration of the end effector. The retaining element 54 can also have a variety of configurations, but in the illustrated embodiment the retaining element 54 is in the form of a hollow ring or cylinder.

Figure 6A:
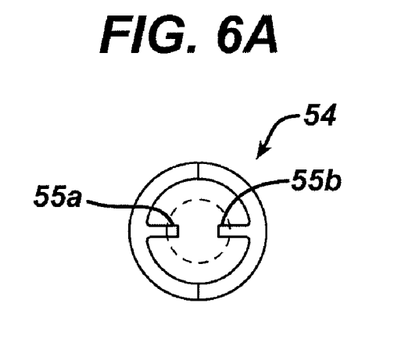
FIG. 6A is a cross-sectional view of a retaining element for retaining an end effector in a chamber of a cartridge.
Figure 6B:
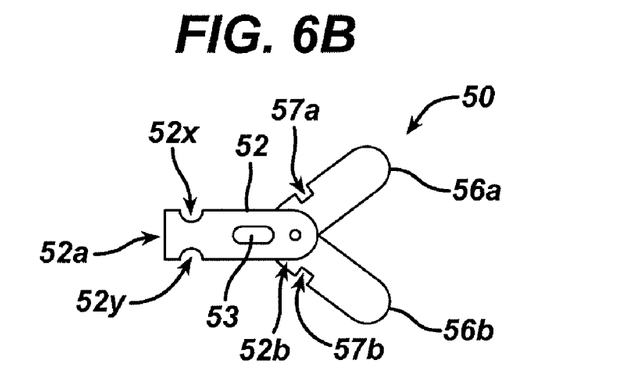
FIG. 6B is a side view of one embodiment of an end effector configured to slidably mate to the retaining element of FIG. 6A.
Figure 7A:
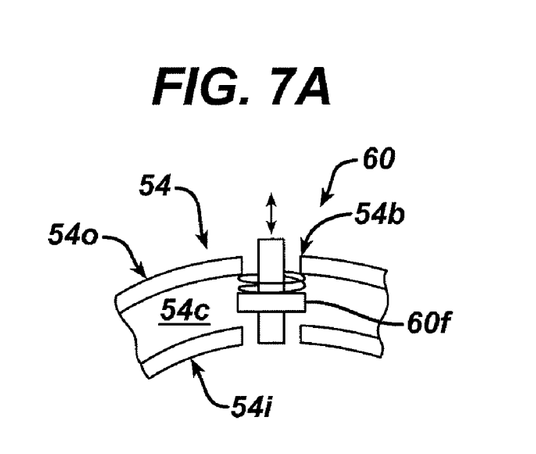
FIG. 7A is a side partially cross-sectional view of one embodiment of a pin and biasing element for releasably mating the retaining element of FIG. 6A to a chamber in a cartridge.
Figure 7B:
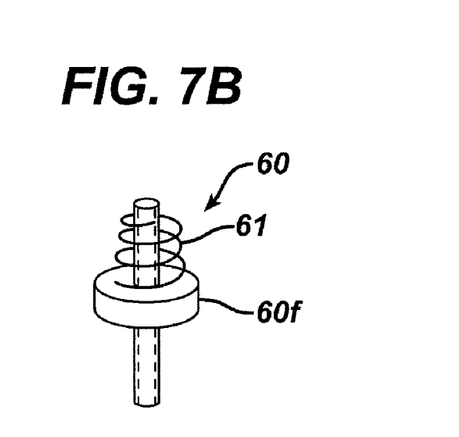
FIG. 7B is a side perspective view of the pin and biasing element of FIG. 7A.

In order to retain the end effector 50 in a chamber, e.g. chamber 14a in cartridge 14, the retaining element 54 can include one or more pins movably disposed therein. FIGS. 5A-5D illustrate two pins 60, 62 disposed within the retaining element 54. Each pin 60, 62 can be movable between an engaged position, in which the pin 60, 62 protrudes outward from the retaining element 54 and engages a bore 646, 66 in the chamber 14a to lock the end effector 50 in the chamber 14a, and a disengaged or released position, in which the pin 60, 62 is retracted into the retaining element 54 to allow the end effector 50 to be released from the chamber 14a. FIGS. 7A and 7B illustrate a portion of the retaining element 54 and one of the pins, e.g., pin 60, in more detail. As shown, the retaining element 54 is hollow and defines a cavity 54c formed therein between inner and outer sidewalls 54i, 54o thereof. The retaining element 54 can also include a bore or opening 54b extending therethrough between the inner and outer sidewalls 54i, 54o thereof for receiving opposed ends of the pin 60. A flange 60f can be formed on the pin 60 and disposed within the cavity 54c in the retaining element 54 to prevent removal of the pin 60 from the retaining element 54. As further shown in FIGS. 7A and 7B, the pin 60 can include a biasing element, such as a biasing spring 61, disposed therearound and adapted to bias the pin 60 toward the clevis 52 (FIGS. 5A-5D and 6B).

Figure 5A:
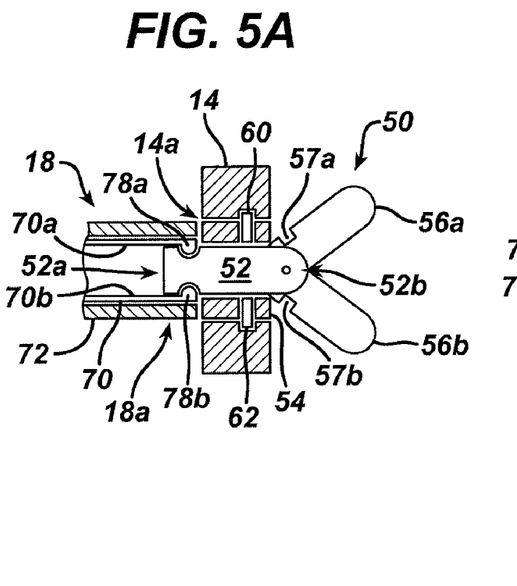
FIG. 5A is a side cross-sectional view of one embodiment of an end effector disposed within a chamber in a cartridge, showing an insertion device mated to the end effector.
Figure 5B:
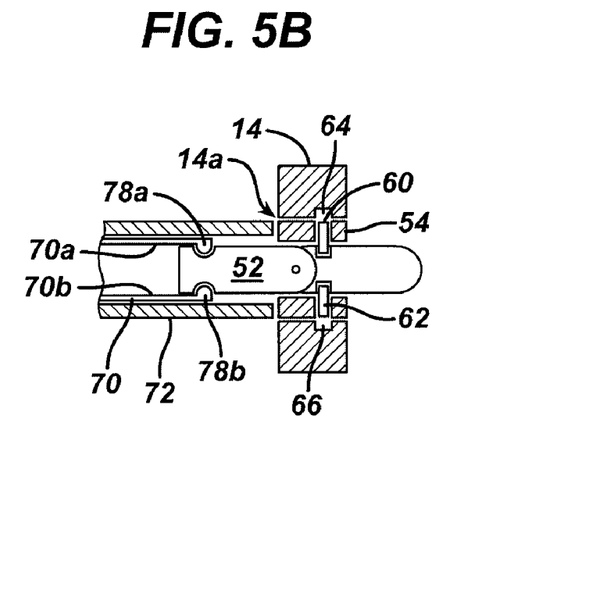
FIG. 5B is a side cross-sectional view of the end effector and cartridge of FIG. 5A, showing the insertion device retracted proximally to disengage the end effector from the chamber in the cartridge.

In use, when the end effector 50 is disposed within the chamber 14a in the cartridge 14, the clevis 52 can force each pin 60, 62 in the retaining element 54 into the bore 64, 66 formed on an inner surface of the cartridge chamber 14a, as shown in FIG. 5A. As a result, the end effector 50 will be locked within the chamber 14a. In order to release the end effector 50, i.e., to move the pins 60, 62 out of the bores 64, 66 in the chamber 14a, the clevis 52 can be slidably retracted in a proximal direction relative to the retaining element 54 to allow the biasing spring 61 to move the pins 60, 62 into corresponding bores or detents formed in the end effector. FIGS. 5A and 6B illustrates pockets 57a, 57b formed in a proximal end of each jaw 56a, 56b of the end effector 50, and FIG. 5B illustrates the clevis 52 moved proximally relative to the retaining element 54 such that the pins 60, 62 extend into the pockets 57a, 57b in the jaws 56a, 56b. As a result, the pins 60, 62 are retracted into the retaining element 54 and thus allowing the retaining element 54, and thus the end effector 50, to be removed from the chamber 14a.

In order to allow the clevis 52 to be retracted relative to the retaining element 54, the clevis 52 and retaining element 54 can be slidably mated to one another. While various techniques can be used to allow slidable movement between the clevis 52 and the retaining element 54, in the illustrated embodiment the clevis 52 has an elongate slot 53 extending therethrough between opposed sides thereof, as illustrated in FIG. 6B. The inner surface of the retaining element 54 includes opposed arms 55a, 55b formed thereon and adapted to extend into the elongate slot 53. The arms 55a, 55b will slide longitudinally within the slot 53, thereby allowing the clevis 52 to slide longitudinally relative to the retaining element 54. The arms 55a, 55b and slot 53 will also prevent removal of the clevis 52 from the retaining element 54, thereby allowing the retaining element 54 to retain the clevis 52 within the cartridge chamber 14a.

Movement of the clevis 52 relative to the retaining element 54 can be achieved using the instrument shaft 18. The particular configuration of the instrument shaft 18 can vary, as previously discussed, but in an exemplary embodiment the instrument shaft 18 includes inner and outer members 70, 72. As shown in FIGS. 5A-5D, the inner and outer members 70, 72 can each have a cylindrical hollow configuration, and the inner member 70 can be adapted to engage the clevis 52 while the outer member 72 abuts against the retaining element 54 to allow the inner member 70 to move the clevis 52 relative to the retaining element 54. Various engagement techniques can be used to engage the clevis 52 with the inner member 70. In the illustrated embodiment, the inner member 70 includes opposed arms 70a, 70b formed on a distal end thereof and adapted to flex relative to one another. Each arm 70a, 70b can include a protrusion 78a, 78b formed on a distal end thereof and adapted to extend into a corresponding detent 52x, 52y (FIG. 6B) formed in a proximal end of the clevis 52, as shown. In use, the flexible arms 70a, 70b can be positioned around the clevis 52 to cause the protrusions 78a, 78b to extend into and engage the detents 52x, 52y in the clevis 52. The inner member 70 can then be retracted relative to the outer member 72 to move the clevis 52 proximally relative to the retaining element 54, which is held in place by the outer member 72. As the clevis 52 moves proximally, the jaws 56a, 56b will close as they are pulled in the to retaining element 54, thus allowing the pins 60, 62 in the retaining element 54 to extend into the pockets 57a, 57b in the jaws 56a, 56b to thereby release the end effector 50 from the chamber 14a. The outer member 72 will also be positioned around the flexible arms 70a, 70b on the inner member 70 to prevent the protrusions 78a, 78b from becoming disengaged with the detents 52x, 52y. The distal end 18a of the instrument shaft 18 will thus be locked onto the clevis 52.

Figure 5C:
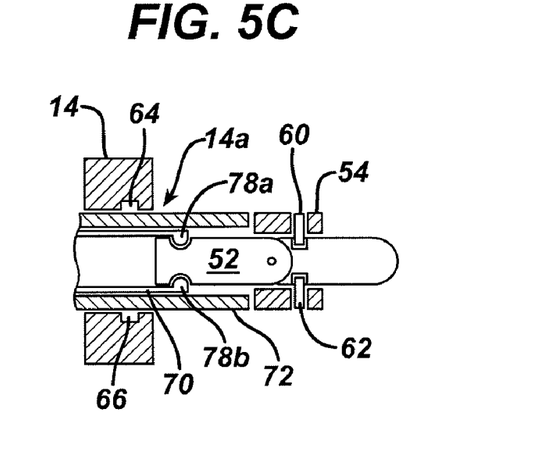
FIG. 5C is a side cross-sectional view of the end effector and cartridge of FIG. 5B, showing the insertion device advanced distally to remove the end effector from the chamber in the cartridge.
Figure 5D:
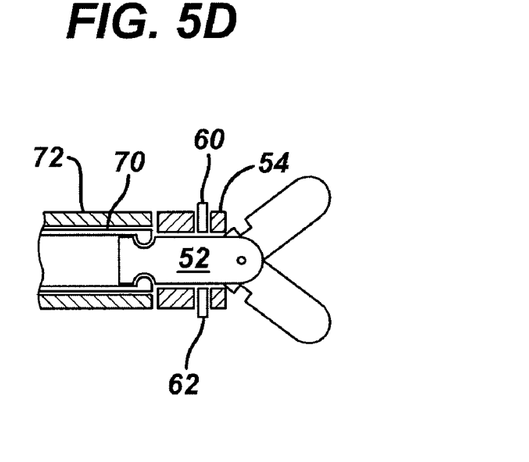
FIG. 5D is a side cross-sectional view of the end effector and cartridge of FIG. 5C, showing the insertion device retracted proximally to return the end effector to the chamber in the cartridge.

Once the instrument shaft 18 is locked onto the clevis 52 and the end effector 50 is released from the chamber 14a (i.e., the pins 60, 62 are retracted into the retaining element 54 and extend into the jaw pockets 57a, 57b) as shown in FIG. 5B, the outer member 72 can be advanced distally to push the retaining element 54, and thus the end effector 50, out of the chamber 14a, as shown in FIG. 5C. The end effector 50 an now be used to perform a surgical procedure. For example, the inner member 70 can be advanced distally relative to the outer member 72 to push the clevis 52 distally. As a result, the jaws 56a, 56b will be advanced distally out of the retaining element 54 and can thus open to receive tissue therebetween, as shown in FIG. 5D. While not shown, the jaws 56a, 56b can include a biasing element that biases the jaws 56a, 56b to the open position when the jaws 56a, 56b are moved out of the retaining element 54. The first time that the inner member 70 is advanced distally, the biasing spring 61 will cause the pins 60, 62 to slide out of the pockets 57a, 57b in the jaws 56a, 56b and to protrude from the retaining element 54. The flange 60f will prevent the pins 60, 62 from falling out of the retaining element 54. The inner member 70 can be repeatedly moved distally to close the jaws 56a, 56b and proximally to open the jaws 56a, 56b to thereby perform a surgical procedure.

Once the procedure is complete, the end effector 50 can be returned to its original chamber 14a by reversing the procedure used to remove the end effector 50. In particular, the inner member 70 can be retracted proximally relative to the outer member 72 to allow the pins 60, 62 to slide into the pockets 57a, 57b in the jaws 56a, 56b as the jaws 56a, 56b are closed by the outer member 72. The inner and outer members 70, 72 can then be retracted relative to the cartridge 14 to pull the entire end effector 50 into the chamber 14a. Once the end effector 50 is positioned within the chamber 14a, the inner member 70 can be advanced distally to force the pins 60, 62 to extend out of the retaining element 54 and into the bores 64, 66 formed in the chamber 14a. The outer member 72 can then be retracted proximally relative to the inner member 70 to release the flexible arms 70a, 70b, thereby allowing the flexible arms 70a, 70b to be removed from engagement with the clevis 52. Once the end effector 50 is free from the instrument shaft 18, the cartridge 14 can be rotated to position another end effector disposed within another chamber into alignment with the instrument shaft 18. The shaft 18 can then be manipulated as previously described to engage the second end effector, release and remove the end effector from the chamber, perform a surgical procedure, and return the end effector to the chamber. This can be repeated for each end effector retained within the cartridge, thereby allowing multiple end effectors to be used during the same procedure without the need to remove the insertion device and instrument shaft from the patient's body.

The devices disclosed herein can be provided as a kit containing one or more cartridges having and one or more surgical end effectors. The cartridge(s) can be configured to be removably mated to an insertion device, thus allowing the surgeon to select the desired cartridge. The surgeon can also select the desired end effectors and load them into the cartridge prior to the procedure.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A modular endoscopic surgical device, comprising:
an insertion device having a cartridge movably disposed on a distal portion thereof, the cartridge having a plurality of chambers formed therein;
a plurality of surgical end effectors, each surgical end effector being disposed within a chamber in the cartridge; and
an instrument shaft adapted to interchangeably mate with the plurality of surgical end effectors, the instrument shaft having a first member adapted to selectively engage a surgical end effector disposed within a chamber, and a second member, the first member being adapted to translate relative to the second member to displace said surgical end effector from the chamber,
wherein each end effector is movable within the chamber between a first position in which at least one pin on the end effector extends into at least one bore formed in the chamber to retain the end effector in the chamber, and a second position in which the at least one pin on the end effector is retracted into the end effector to allow the end effector to be released from the chamber.

2. The device of claim 1, wherein the instrument shaft is longitudinally slidably coupled to the insertion device.

3. The device of claim 2, wherein the instrument shaft is disposed through an accessory channel coupled to the insertion device.

4. The device of claim 1, wherein the insertion device comprises an endoscope.

5. The device of claim 1, wherein movement of the first and second members relative to one another is adapted to actuate the surgical end effector.

6. The device of claim 1, wherein the cartridge is rotatably disposed around a distal portion of the insertion device.

7. The device of claim 6, further comprising an actuator movably coupled to the insertion device and adapted to rotate the cartridge relative to the insertion device to selectively position a chamber in alignment with the instrument shaft.

8. The device of claim 1, wherein the cartridge is longitudinally slidable along a longitudinal axis of the insertion device.

9. The device of claim 1, wherein each of the plurality of end effectors includes a clevis, and wherein the first member is adapted to engage a proximal portion of the clevis.

10. The device of claim 9, wherein the second member is movable between a proximal position in which the second member is retracted relative to the first member to allow the first member to be disengaged from an end effector, and a distal position in which the second member is advanced over the first member to lock the first member into engagement with an end effector.

11. The device of claim 1, wherein each end effector includes a clevis and a retaining element slidably mated to and disposed around the clevis, and wherein the at least one pin is disposed within at least one thru-hole extending through the retaining element.

12. The device of claim 11, wherein the at least one pin is biased into the end effector.

13. The device of claim 1, wherein each end effector has an engagement mechanism movable between a locked position, in which the engagement mechanism extends outward from the end effector to retain the end effector within the chamber, and a released position in which the engagement mechanism is retracted into the end effector to release the end effector from the chamber.

14. A modular endoscopic surgical device, comprising:
an elongate shaft having a cartridge coupled thereto, the cartridge having a plurality of chambers formed therein;
a plurality of end effectors disposed within the plurality of chambers, each end effector having an engagement mechanism movable between a locked position, in which the engagement mechanism extends outward from the end effector to retain the end effector within the chamber, and a released position in which the engagement mechanism is retracted into the end effector to release the end effector from the chamber; and
an instrument shaft adapted to selectively engage each of the plurality of end effectors and to effect movement of the end effector relative to the chamber to cause the engagement mechanism to move between the locked and released positions.

15. The device of claim 14, wherein the cartridge is rotatably disposed around a distal portion of the elongate shaft.

16. The device of claim 14, wherein the cartridge is longitudinally slidable along a longitudinal axis of the elongate shaft.

17. The device of claim 14, wherein the elongate shaft comprises an endoscope.

18. The device of claim 14, wherein the instrument shaft includes an inner tube adapted to engage an end effector, and an outer tube slidably disposed over the inner tube and adapted to lock the inner tube into engagement with the end effector.

19. The device of claim 18, wherein, when the inner tube is in locked engagement with an end effector, the inner tube is adapted to move relative to the outer tube to cause the engagement mechanism on the end effector to move between the locked and released positions.

20. The device of claim 18, wherein one of the end effectors includes opposed jaws pivotally coupled to one another and adapted to receive tissue therebetween.

* * * * *